United States Patent [19]
Ono et al.

[11] Patent Number: 5,163,317
[45] Date of Patent: Nov. 17, 1992

[54] APPARATUS FOR MEASURING STRESS OF VISCOELASTIC MATERIAL

[75] Inventors: Shigeki Ono; Noboru Tsukahara; Kosaku Otani, all of Tokyo, Japan

[73] Assignees: Bridgestone Corporation; K.K. Toyo Seiki Seisakusho, both of Tokyo, Japan

[21] Appl. No.: 673,547

[22] Filed: Mar. 22, 1991

[30] Foreign Application Priority Data

| Mar. 26, 1990 | [JP] | Japan | 2-73245 |
| Mar. 26, 1990 | [JP] | Japan | 2-73246 |
| Nov. 9, 1990 | [JP] | Japan | 2-302758 |

[51] Int. Cl.⁵ ............................................. G01N 11/00
[52] U.S. Cl. .................................. 73/54.32; 73/54.39
[58] Field of Search ............. 73/59, 60, 843, 846, 73/841, 54.32, 54.34, 54.39; 374/47, 48

[56] References Cited

U.S. PATENT DOCUMENTS

| 2,037,529 | 5/1936 | Mooney | 73/843 |
| 2,737,805 | 1/1956 | Blumenbaum | 73/843 |
| 3,479,858 | 11/1969 | Umeno et al. | 73/843 |
| 3,535,914 | 10/1970 | Veith et al. | 73/843 |
| 3,818,751 | 6/1974 | Karper et al. | 73/843 |
| 4,343,190 | 8/1982 | Danko | 73/60 |
| 4,421,424 | 12/1983 | Price et al. | 374/48 |
| 4,552,025 | 11/1985 | Barker et al. | 73/846 |
| 4,601,195 | 7/1986 | Garritano | 73/60 |
| 4,829,830 | 5/1989 | Tosaki | 73/847 |
| 4,878,379 | 11/1989 | Deer | 73/60 |
| 4,953,406 | 9/1990 | Putman | 73/843 |
| 5,079,956 | 1/1992 | Burhin et al. | 73/60 |

FOREIGN PATENT DOCUMENTS

| 1648526 | 3/1967 | Fed. Rep. of Germany . | |
| 0115939 | 9/1981 | Japan | 73/60 |
| 0003263 | 5/1988 | PCT Int'l Appl. | 73/60 |
| 671634 | 3/1986 | Switzerland . | |
| 1241332 | 8/1971 | United Kingdom . | |
| 2212269 | 10/1987 | United Kingdom . | |

*Primary Examiner*—Michael Razavi
*Assistant Examiner*—Raymond Y. Mah
*Attorney, Agent, or Firm*—Sughrue, Mion, Zinn, Macpeak & Seas

[57] ABSTRACT

An apparatus for measuring stress of viscoelastic material in which a rotational die and a torque detecting die are provided, an outer cylindrical die is provided around the torque detecting die, the diameter of the rotational die is arranged to be larger than the diameter of the outer cylindrical die, and the surface forming one part of a sample chamber has such configuration that a slipping of the sample contained in the sample chamber is prevented, so that a shearing speed having no disorder can be given to the sample mounted all over a surface, forming the sample chamber, of the torque detecting die. Furthermore, in the apparatus according to the invention, since the torque detecting die and the outer cylindrical die provided therearound are arranged to be rotated in the same direction by the same angle in accordance with the shearing stress given by the sample, it is possible to detect correctly the counter-torque given by the sample without being influenced by a seal provided between the torque detecting die and the outer cylindrical die.

22 Claims, 19 Drawing Sheets

FIG_2A PRIOR ART
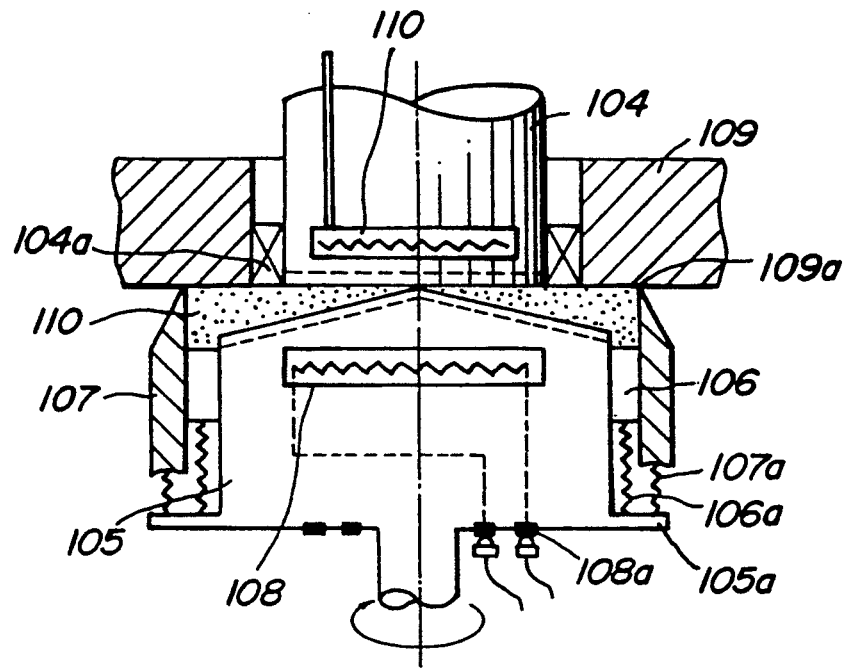
FIG_2B PRIOR ART
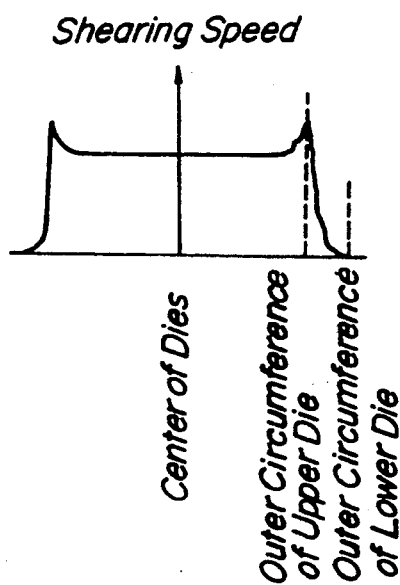

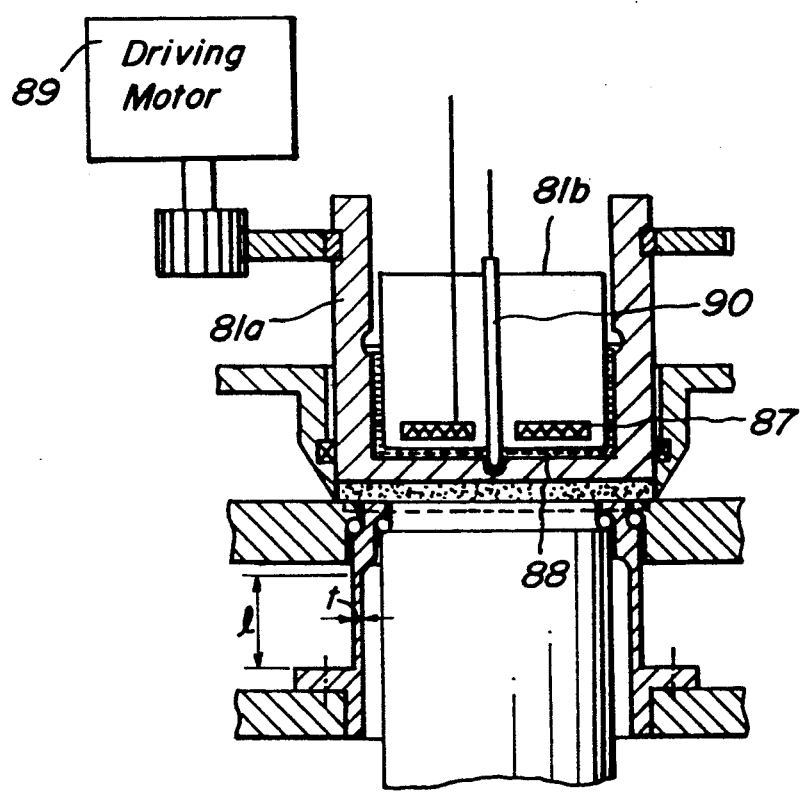
FIG_6

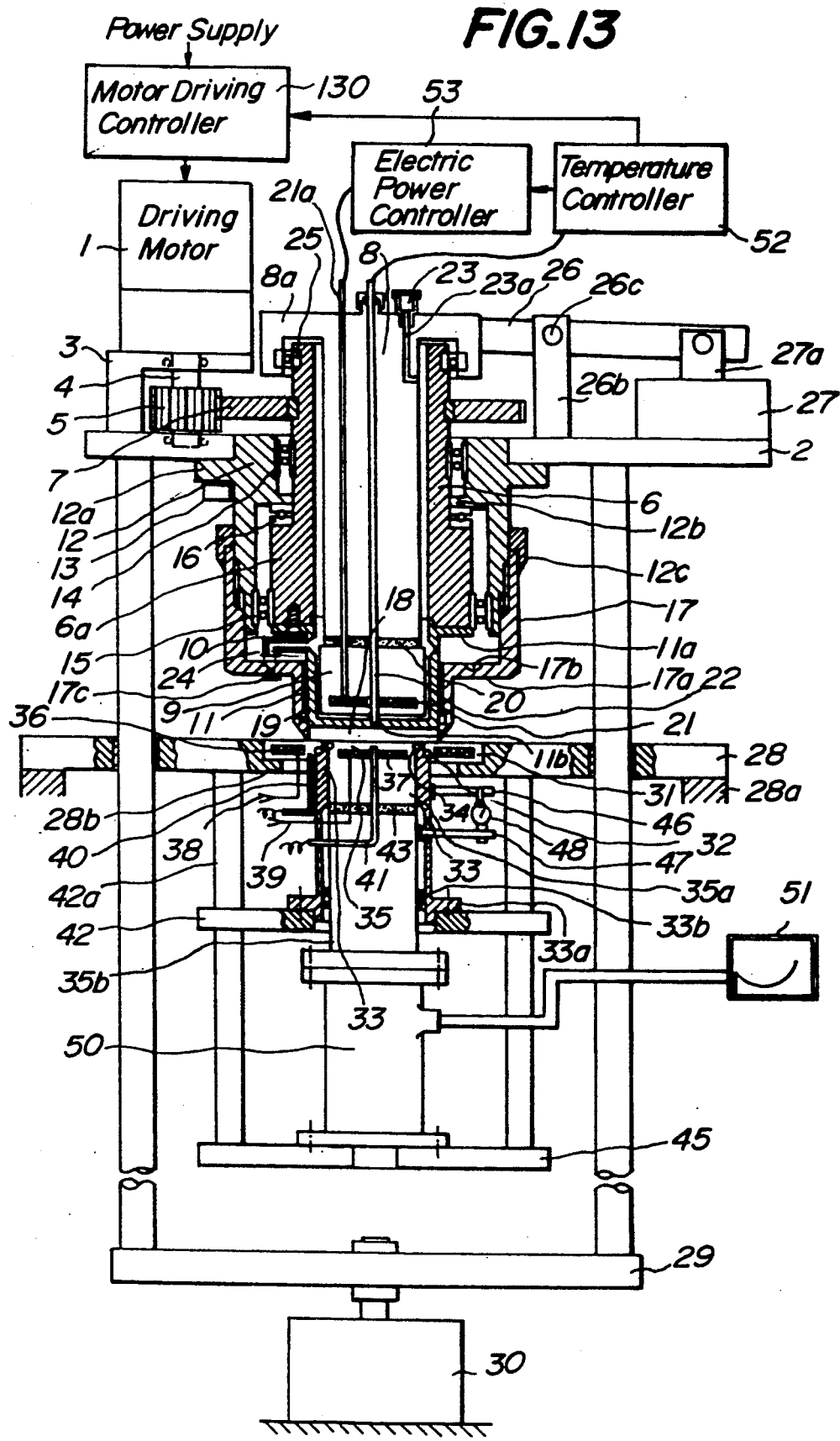

FIG._15A
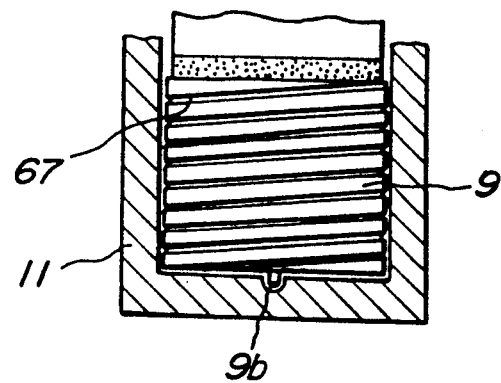
FIG._15B
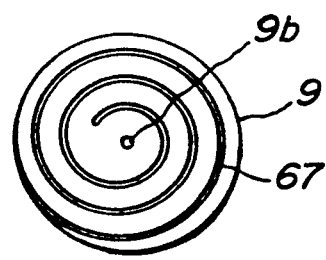

FIG._22
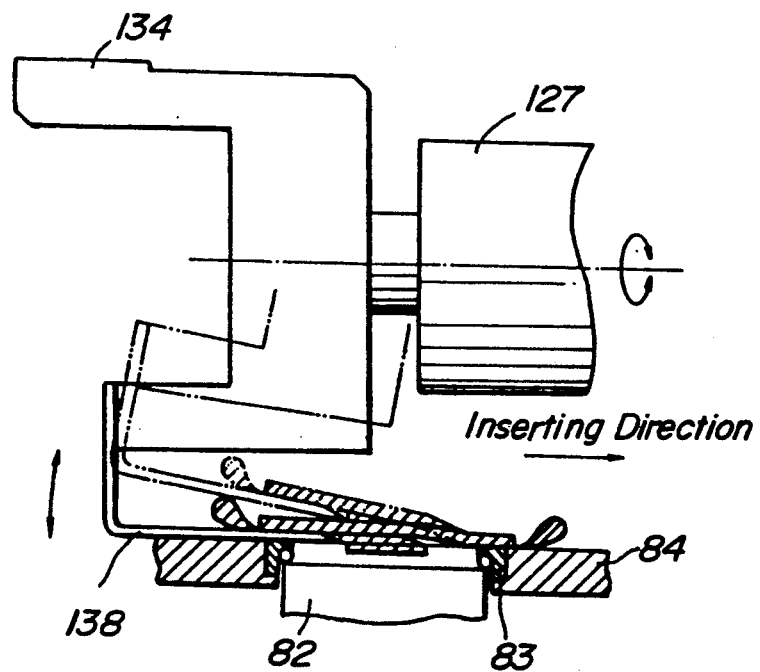
FIG._23
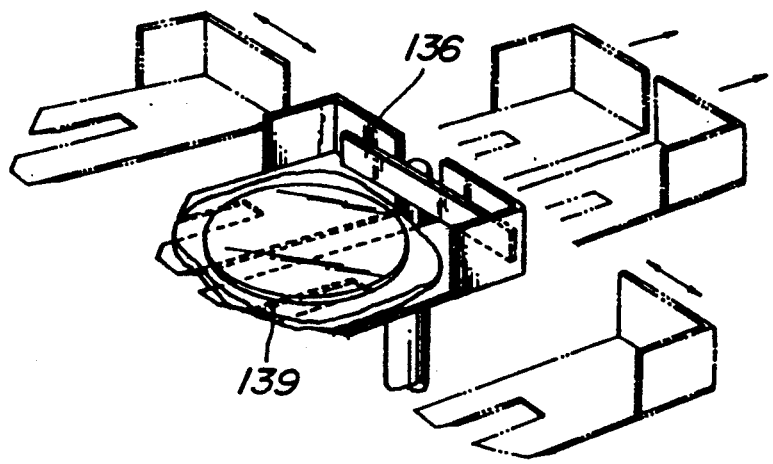

APPARATUS FOR MEASURING STRESS OF VISCOELASTIC MATERIAL

BACKGROUND OF THE INVENTION

1) Field of the Invention

The present invention relates to an apparatus for measuring stress of viscoelastic material such as rubber, by which the stress generated in the viscoelastic material when a shear is continuously given thereto can be measured.

2) Prior Art Statement

The performance of rubber products is determined and influenced by the characteristics of raw material and rubber compounded thereinto, such as plasticity, viscosity and elasticity. Therefore, when producing, evaluating, developing and researching an elastomer element or a composition of rubber, it is necessary to measure such characteristics of the materials and obtain exact information concerning processing efficiency thereof.

M. Mooney invented a rotary disc type viscometer 60 years ago which is used for measuring a viscocity of viscoelastic material. This viscometer is widely used for obtaining indices of processing efficiency of the elastomer such as rubber; in the rubber industry. The viscometer is standardized by ASTM and ISO, etc. throughout the world. In Japan, it is standardized in JIS K6300 such that the physical property of non-vulcanized rubber is measured by using the Mooney viscometer.

FIG. 1A is a cross-sectional view showing the Mooney viscometer. The Mooney viscometer is a so-called rotor type viscometer, in which a rotor 101 and sample material are arranged in a cylindrical sample chamber 103 which is formed by an upper die 102a and a lower die 102b. The rotor 101 is rotated in one direction by a motor (not shown) to measure a counter-torque which acts on a shaft 101a of the rotor 101. The Mooney viscometer is widely and generally used and has improved over time. However, even in the improved viscometers, the rotor is always used. Therefore, the Mooney viscometer has such problems that: ① the measurement data is varied due to a bending of the rotor shaft 101a; ② generally two or more rotors are used in one Mooney viscometer apparatus in order to increase operational efficiency and thus the measurement data is varied between or among the plurality of rotors; ③ when the Mooney scorching test is conducted, particularly, the side surfaces and the upper surface of the rotor 101 are damaged when the sample is removed from the rotor after the test has been finished, so that the measurement data is varied; and ④ the measurement data is varied due to an aging of an O ring (not shown), which is arranged on the rotor shaft 101a for the purpose of sealing and due to a friction force generated between the O ring and the rotor shaft 101a. Therefore, in order to keep measurement accuracy of the Mooney viscometer, it is necessary to increase the number of steps for maintenance of the viscometer.

By the Mooney viscometer, a rotation number of the rotor 101 and a value of counter torque, which acts on the rotor shaft 101a, are measured. The method is widely used in that the rotation number and the value of counter-torque are exchanged into a shearing velocity ($\gamma$) and a shearing stress (s) to evaluate the processing efficiency of the sample. In this case, it is necessary to certainly give a shearing force to the sample without slipping of the rotor 101 and to correctly detect the shearing stress which acts on the sample as the counter torque. FIG. 1B is a graph showing, a shearing velocity ($\gamma$) given to the sample, which is measured in the Mooney viscometer shown in FIG. 1. In the graph of FIG. 1B, the abscissa R represents a distance from a center point of the rotor 101. The sample contained in the sample chamber 103 is divided into characteristic regions of a, b and c, as shown in FIG. 1C, to measure separately the shearing velocity and the shearing stress in each region. On inner surfaces of the upper and lower dies 102a and 102b and all of outer surface of the rotor, a plurality of grooves are formed in order to prevent slipping of the sample, so that the rotation of the rotor certainly gives a shear to the sample and the shearing stress generated in the sample thereby is transmitted to the rotor shaft 101a as the counter torque. However, in the apparatus shown in FIG. 1C, it is impossible to detect the shearing stress of the sample arranged in the region c. Because, there has been no formula to exchange the rotation number of the rotor shaft 101 into the shearing velocity concerning the sample arranged in the region c; and since the sample arranged in the region c is not in contact with the rotor 101 directly it can be assumed that the shear which acts on the sample c does not contribute to the torque directly.

There is disclosed a conical type rotating viscometer, i.e. a rotorless type viscometer, in Japanese Patent Publication No. 50-26101. FIG. 2A is a cross-sectional view showing a principle construction of the rotorless type viscometer. The rotorless type viscometer comprises an upper die 104 on the surface of which a plurality of grooves are formed in order to prevent the slip of the sample, a lower rotational die 105, a seal 104a made of elastic material arranged between the upper die 104 and an upper fixed die 109, an annular ring 106 arranged around the outer circumference of the lower rotational die 105, and a lower die protection ring 107 arranged around the annular ring 106. It should be noted that these members are arranged in a concentrical manner. The annular ring 106 and the lower die protection ring 107 are arranged to be movable in upper and lower directions by means of springs 106a and 107a whose end portions are secured to a flange portion 105a of the lower rotational die 105.

A heater 108 is embedded in the lower rotational die 105 and to the heater 108 electric power is supplied via slip rings 108a. A top portion of the lower die protection ring 107 is engaged with an angular groove 109a which is formed on the bottom surface of the upper fixed die 109. As shown in FIG. 2A, the sample chamber 110 is formed by the inner surface of the lower die protection ring 107, the bottom surface of the upper die 104, the bottom surface of the upper fixed die 109, the upper surface of the annular ring 106, and the upper surface of the lower rotational die 105. The shear is given to the sample contained in the sample chamber 110 by rotating the lower rotational die 105 and the lower die protection ring 107; the torque generated in the sample is measured by the upper die 104.

In order to make an elasticity transformation torque as small as possible, a portion of the surface of the seal 104 arranged around the outer circumference of the upper die, i.e. die for detecting the torque, is exposed to the sample chamber 110. However, the surface of the seal 104 exposed to the sample chamber 110 is not formed such that the slip of the sample can be prevented, while the protection ring 106 is arranged to be rotatable being accompanied with the rotation of the lower rotational die 105. Therefore, when the lower rotational die 105 is rotated, the sample arranged under the outer circumferential portion of the upper die 104 and the upper fixed die 109 suddenly slips, so that the shearing velocity in the vicinity of the outer circumference of the upper die 104 falls into disorder. FIG. 2B is a graph showing the velocity of the shear generated in the sample contained in the sample chamber 110 of the apparatus shown in FIG. 2A. It is clear from FIG. 2B that the counter torque in accordance with the shearing stress being influenced by the slip of the sample arranged under the exposed portion of the seal 104a exposed to the sample chamber 110 is measured by the upper die 104. The slipped sample is not given a shear to the upper die 104 but rotated at the same rotating speed as that of the lower rotational die 105.

As a result, the shearing velocity of the sample arranged in the vicinity of the outer circumference portion of the upper die 104 is high and an apparent large counter-torque is measured by the upper die 104. Further, the slippage amount of the sample cannot be specified because it is also varied in accordance with a tackiness between the sample and the inner wall of the sample chamber 110.

According to linear elastic theory, the counter torque T generated in the torque detecting die is represented by the formula $T \propto R^3$ in a conical type die or the formula $T \propto R^4$ in a parallel disc type die; wherein R represents a radius of the torque detecting die. As is clear from this, since the outer circumferential portion of the torque detecting die largely contributes to the counter-torque generated therein, the disorder of the shearing velocity in the outer circumferential portion of the torque detecting die would influence the torque to be detected.

Furthermore, in this apparatus, the torque detecting die is rotated by the shearing stress given by the sample; the force to rotate the torque detecting die is detected as the torque. However, the value of the torque detected by the torque detecting die does not include a friction torque generated between the outer circumferential surface of the torque detecting die 104 and the inner surface of the seal 104a and an elasticity transformation torque of the seal 104a. Therefore, the torque detected by the torque detecting die does not show the correct value.

Furthermore, the sealing effect of the seal 104a deteriorates due to the heat deterioration of the material thereof when long time has been passed. Additionally, the friction torque and the elasticity transformation torque are apt to be increased, accordingly. Moreover, since the increased values of the friction torque and the elasticity transformation torque cannot be specified, it is difficult to correct the deteriorated value.

In the Japanese Patent Publication No. 60-25735, there is disclosed another rotorless type hardness measuring apparatus. FIG. 3A is a cross-sectional view showing the rotorless type hardness measuring apparatus. The apparatus comprises an upper die 111, a lower die 112, an upper fixed die 113 and a lower fixed die 114. A sample chamber 115 is formed by the lower surface of the upper die 111, the upper surface of the lower die 112, the lower surface of the upper fixed die 113 and the inner surface of the lower fixed die 114. It should be noted that there are formed a plurality of grooves on the lower surface of the upper die 111 and the upper surface of the lower die 112. A sample is contained in the sample chamber 115; the lower die 112 is rotated about a rotating shaft of the lower die 112. Therefore, the shear having an amplitude of small angle is repeatedly given to the sample, and thus the disorder due to the slip of the sample does not generated so much. However, when the lower die 112 is rotated in one direction, i.e. the shear in one direction is given to the sample continuously, the shearing value is increased as time goes on and the sample arranged in the vicinity of an O ring 116, which is arranged between the upper die 111 and the upper fixed die 113, is slipped to the outer side, so that the shearing velocity in the vicinity of the seal portion 116 falls, as shown in FIG. 3B.

In the above mentioned measurement apparatuses, there are provided heating devices in the upper and lower dies in order to keep the sample chamber at an appropriate temperature. One example of the heating device is shown in FIG. 2A. In the apparatus shown in FIG. 2A, heating devices 108 and 110 are embedded in the upper and lower die 104 and 105, respectively, and the temperature in the sample chamber 110 is controlled by these heaters. Since the heating device 108 provided in the rotational die 105 is rotated in accordance with the rotation of the lower die 105, slip rings 108a are generally used to supply electric power to the heating device 108. Additionally, a temperature detector (not shown) is generally arranged inside of the lower die 105, and the temperature signal thereof is generally derived via slip rings 108a.

However, in the conventional apparatus there are many problems such that electric contacts at the slip ring portions sometimes deteriorate, the contact register is varied and electric noise is generated, due to corrosion of the slip ring portion, dust adhered on the slip ring portion or abrasion of the carbon brush. And thus the deteriorated electric contact, the decrease of the contact register and the electric noise sometimes disable the apparatus and decrease the accuracy of temperature controlling.

Further, in the conventional apparatus, the heating devices are directly embedded in the upper and lower dies, so that the upper and lower dies are directly heated up by the heating devices. Therefore, the temperature of these dies are not even; that is to say, the temperature of the portion close to the heating device becomes high and that of the portion far from the heating device becomes low. The unevenness of the temperature of the dies results that the measurement data of the viscocity of the sample is varied because the temperature of the sample heated up by the dies becomes heated up in an uneven manner.

In Japanese Patent Publication No. 60-120253, there is disclosed an apparatus in which the sample is automatically mounted in the sample chamber and automatically removed therefrom. However, if the automatic mounting and removing system is applied to detect the hardness of a non-vulcanized rubber or a semi-vulcanized rubber, it is difficult to remove the sample, i.e. non-vulcanized or semi-vulcanized rubber, from the sample chamber after the measurement of the hardness of the sample has been finished, because the non-vulcanized or semi-vulcanized rubber has a high viscosity.

SUMMARY OF THE INVENTION

The first purpose of the present invention is to provide an apparatus for measuring a stress of viscoelasticity material, such as rubber, in which the velocity of shear which acts on the sample is not disordered on or under the entire surface of the torque detecting die.

FIG. 4A is a schematic view showing the first aspect of the invention. In order to carry out the first purpose, the apparatus comprises an upper die (81) and a lower die (82), which are arranged on the same rotation axis in an opposite manner; rotating means for rotating either of said upper die (81) or said lower die (82) (the upper die is rotated in the apparatus shown in FIG. 4A); detecting means for detecting counter torque which acts on the other die (the lower die detects the torque in the apparatus shown in FIG. 4A):

an outer cylindrical die (83) being arranged on an outer circumference of the torque detecting die (lower die 82);

a diameter of the rotational die (upper die 81) rotated by said rotating means being arranged to be larger than a diameter of said outer cylindrical die (83);

a fixed die (17) being arranged on an outer circumference of said rotational (upper die 81);

sample chamber being formed by a bottom surface of the upper die (81), an upper surface of the lower die 82, an upper surface of the outer cylindrical die (83) and an inner surface of the fixed die (17); and said bottom surface of the upper die (81), said upper surfaces of the lower die (82) and the outer cylindrical die (83) being formed such that a sample contained in the sample chamber does not slip when the rotational die (81) is rotated to give a shear to the sample.

In FIG. 4A, the numerical number 84 denotes a lower fixed die; 86 a seal arranged between the outer cylindrical die 83 and the lower fixed die 84. In the apparatus according to the first invention of the present application, on the outer circumference of the lower die 82 (torque detecting die), whose upper surface is formed to prevent the sample contained in the sample chamber from slippage, is arranged the outer cylindrical die 83, and on the inner surface of the outer cylindrical die 83; the upper surface of the outer cylindrical die 83, forming of one part of the sample chamber, is also formed to prevent slipping of the sample; the diameter of the upper rotating die 81 is arranged to be larger than that of the outer cylindrical die 83; and the upper fixed die 17 is arranged not to be rotated. Therefore, there is generated no slip between the sample and the surface of the torque detecting die 82 in the vicinity of the outer circumference of the torque detecting die 82, so that on the whole area of the upper surface of the lower die 82, i.e. torque detecting die, the velocity of shear which acts on the sample is not fallen into disorder. Thus, the shearing velocity (j), obtained by the formula of $j = \omega r/h$, in which h presents a thickness of the sample, $\omega$ rotating velocity of the rotating die 81 and r a radius of the lower die 82, can be given to the sample without being influenced by the slip of the sample, as shown in FIG. 4B.

FIG. 5A is a schematic view illustrating a principle construction of the second aspect of the invention.

The second purpose of the present invention is to provide an apparatus for measuring a stress of viscoelasticity material, such as rubber, in which the outer cylindrical die (83) and the lower die (82) are arranged to be rotated in the same direction by the same degree according to the shearing stress given by the sample. In the construction illustrated in FIG. 5A, the outer cylindrical die 83 comprises a thin portion 83a, having its thickness t, which is extended in the lower direction by the length l and the lower portion of the outer cylindrical die 83 is secured to a base plate 42 via a flange portion 83b thereof. The numerical reference 85 represents a seal number arranged between the lower fixed die 84 and the outer cylindrical die 83. In the apparatus according to the first aspect of the invention, the lower die 82, i.e. torque detecting die is rotationally deviated by the shearing stress of the sample in accordance with stiffness of the lower die 82, torque detector and members arranged between the lower die 82 and the torque detector. However, in the first aspect shown in FIG. 4A since the outer cylindrical die 83 is directly fixed to the lower fixed die 84, the torque smaller than an actual torque which is influenced by an elastic transformation torque or a friction torque of the seal 86, which is generated in accordance with the rotational deviation of the lower die 82, is detected by the torque detector. Therefore, it is sometimes not possible to detect the correct value of the torque. In contrast thereto, in the apparatus according to the second aspect of the invention of the present application, the outer cylindrical die 83 are arranged such that the outer cylindrical die 83 is rotationally deviated in the same direction by the same angle as the lower die 82. Since the outer cylindrical die 83 is arranged on the base plate 42 such that the length l and the thickness t of the die 83 are adjusted so as to coincident the stiffness of the outer cylindrical die 83 with that of the lower die 82. The lower die 82 and the outer cylindrical die 83 are rotated in a simultaneous manner and thus the proper torque can be detected by the torque detector without being influenced by the seal 86. Further, it is not necessary to expose the seal member, which causes slipping of the sample, to the sample chamber, as the seal member of the conventional apparatus shown in FIG. 2A. The distance between the lower die 82 and the outer cylindrical die 83 can be made small so that the slipping of the sample can be prevented and it is possible to measure the shearing stress generated in the sample more correctly. FIG. 5B is a graph showing a relationship between the shearing velocity and the radii of the dies, forming the sample chamber.

FIG. 6 is a schematic view depicting a principle construction of a third aspect of the invention according to the present application.

The third purpose of the invention is to provide an apparatus for measuring a stress of viscoelasticity material such as rubber, in which an electric power can be supplied to a heating member embedded in the rotational die (upper die 81) without using slip rings.

In the apparatus according to the third invention, the upper die is arranged to be rotatable; the torque is detected by the lower die 82 the upper die comprises a rotational member (81a) and the fixed member which constitute a doubled structure. A heating means (87) is arranged in the fixed member (81b), and the liquid-state or viscostatic-state heating medium 88 is contained in the space between the rotational member (81a) and the fixed member (81b) to control the temperature of the sample in the sample chamber thereby. The temperature of the sample is controlled under a condition that the fixed member (81b) containing the heating means (87) made not made contact with the rotational member (81a). The heating means (87) is provided in the fixed member (81b), that is to say, the heating means is not rotated. Therefore, the slip ring is not necessary to supply electric power to the heating means, and thus there is no problem such as a disorder of the apparatus and an electrical noise, caused by corrosion of the contact portion between the slip ring and the carbon brush, dust which adheres to the contact portion, and abrasion of the carbon brush.

Furthermore, in the construction of the third aspect of the present application, since the rotational member (81a) is indirectly heated up via the heating medium (88), the rotational member (81a) is uniformly heated up. Therefore, the temperature of the sample is uniformly controlled and thus the measurement result is not varied. A liquid, having a given viscocity or a liquid having a low-melting point metal, which has a higher heat conductivity than those of the liquid and the liquid having a given viscocity, are preferably desired as the heating medium. For instance, a silicone oil can be suggested as the liquid having a viscosity; Wood's metal having its melting point of 70° C. such as SK BEND made by Sumitomo Metal Co., Ltd. is suggested as the low-melting point metal. It should be noted that the lower the melting point of the low-melting point metal the better as the heating medium.

In the case that the low-melting point metal is used as the heat medium, if the rotational member 81a is rotated under the condition that the low-melting point metal is still solid, a driving motor 89 would be broken due to an over load, or parts constituting the rotation portion of the rotational member 81a would be broken due to an over stress given to the rotational portion. Therefore, it is preferred to check whether the low-melting point metal has been melted or not. In the third aspect of the invention, a temperature detecting means 90 is provided in the fixed member 81b for controlling the temperature of the rotational member and the temperature detecting means is also used to check whether the low-melting point metal has been melted or not before the motor is started to be driven. Therefore, the third aspect of the invention further comprises a means for controlling the rotational member 81a such that when the low-melting point metal is not melted, the rotational member is not driven until the low-melting point metal is heated up to the melting point of the low melting metal and the low-melting point metal is melted.

Furthermore, in order to increase the heat conductivity between the fixed member and the rotational member and to make the temperature distribution of the sample more uniform, it is preferred to provide plates for agitating the heat medium on the bottom surface of the fixed member or the inner bottom surface of the rotational member.

Moreover, in case the heating medium having a low heat conductivity is used, it is preferred to make a space formed between the rotational member and the fixed member small as soon as possible in order to increase the heat conducting effect. In such a case, it may be possible to form small grooves for containing the heating medium on the side surface and the bottom surface of the fixed member to heat up the rotational driving member substantially uniformly. Additionally, it should be noted that the heating medium also serves as a lubricant, by which the rotational member is rotated smoothly with respect to the fixed member.

The fourth purpose of the invention is to provide an apparatus for measuring stress of viscoelastic material, such as rubber, in which the sample can be automatically mounted on and removed from the sample chamber of the apparatus. In order to carry out this purpose, the apparatus according to the fourth aspect of the invention comprises:

a pair of grooves arranged in an outer circumference of said outer cylindrical die, in an inner circumference of said lower fixed die, or in both the outer circumference of said outer cylindrical die and the inner circumference of said lower fixed die; each couple of grooves being arranged in an opposite manner such that the grooves constitute one part of the sample chamber; and the apparatus comprises a mounting and removing means for automatically mounting and removing a sample on and from the sample chamber.

In the apparatus according to the fourth aspect of the invention, since the grooves are provided in an outer circumference of said outer cylindrical die, in an inner circumference of said lower fixed die, or in both the outer circumference of said outer cylindrical die and the inner circumference of said lower fixed die, the sample is certainly remained in the outer cylindrical die side when the torque has been detected and the upper die is lifted up. Further, when the sample is mounted in the sample chamber, an excess of material sometimes remains on the outer surface of the dies; and in the apparatus according to the fourth aspect, since the contact area of the members arranged in the outer cylindrical die side with respect to the sample is larger than that of the members arranged in the opposite side, the excess material also remains on the member arranged in the outer cylindrical die side.

It is preferred that a member for mounting and removing the sample on and from the sample chamber comprises a plate having a larger area than an area of the torque detecting die, on which the sample is mounted during when the torque detecting test is conducted, in order to clearly remove the sample without leaving remains of the sample in the sample chamber of the apparatus.

As stated, in Japanese Patent Publication No. 60-120253, there is disclosed a system by which the sample is automatically mounted in or removed from the sample chamber of the apparatus. Additionally in the Publication No. 60-120253, there is disclosed an angular inclined groove provided on one of the die. However, if such an inclined groove is provided on the outer cylindrical die side, it is impossible to mount and remove the sample on and from the sample chamber smoothly by using said holding member, because the material to be tested in the apparatus is non vulcanized or semi-vulcanized material which has a very high viscocity.

Furthermore, it is preferred to arrange such that the die forming the bottom surface of the sample chamber is movable in a horizontal direction. It is possible to mount and remove the non-vulcanized sample material on and from the sample chamber easier by the arrangement.

Furthermore, in the fourth aspect of the present application, a serial operations of mounting the sample—detecting the torque—removing the sample—disposing the sample can be automatically conducted by a proper sequence program.

BRIEF DESCRIPTION OF THE DRAWINGS

FIG. 2A is a cross sectional view representing a conventional rotorless rotational conical type viscometer; and FIG. 2B is a graph showing the relationship between a shearing velocity and radii of dies constituting the viscometer;

FIG. 6 is a schematic view showing a principle construction of the third aspect of the apparatus according to the invention;

FIG. 13 is schematic view illustrating a fifth embodiment of the apparatus according to the invention;

FIGS. 15A and 15B are schematic views showing another modification of the heater block;

FIG. 22 is a schematic view depicting a condition where the sample holding plate is inserted between the sample and the lower dies; and FIG. 23 is a schematic view representing a condition where the sample is easily disposed of with the aid of a scraper.

DETAILED EXPLANATION OF THE PREFERRED EMBODIMENTS

Figure 1A:
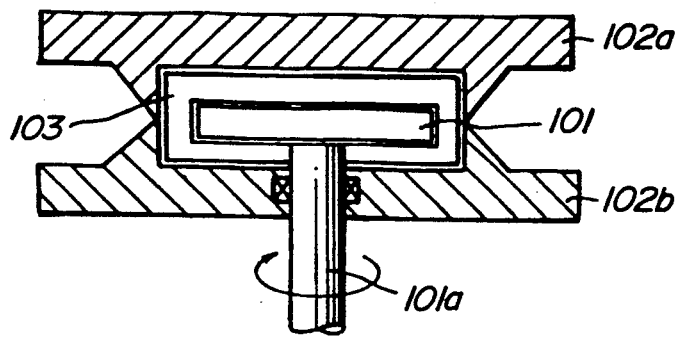
FIG. 1A is a cross sectional view illustrating a principle construction of Mooney viscometer.
Figure 1B:
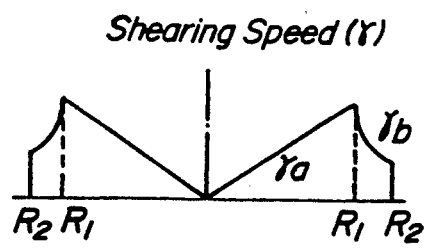
FIG. 1B is a graph showing a relationship between a shearing velocity and a radius of a rotor of the Mooney viscometer.
Figure 1C:
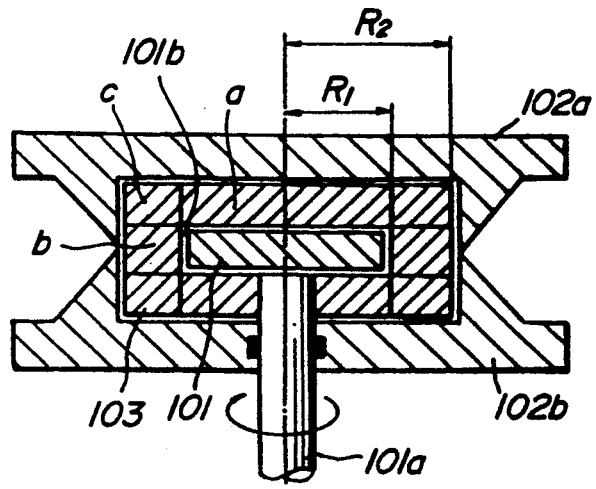
FIG. 1 is a cross sectional view depicting the Mooney viscometer for explaining the relationship between the shearing velocity shown in FIG. 1B and a sample distribution in a sample chamber.
Figure 3A:
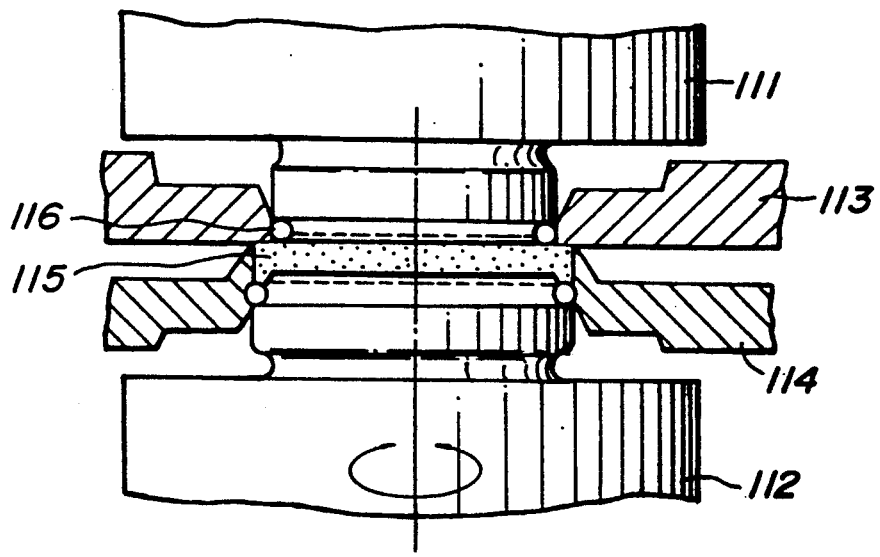
FIG. 3A is a cross sectional view illustrating a conventional rotorless hardness measuring apparatus.
Figure 3B:
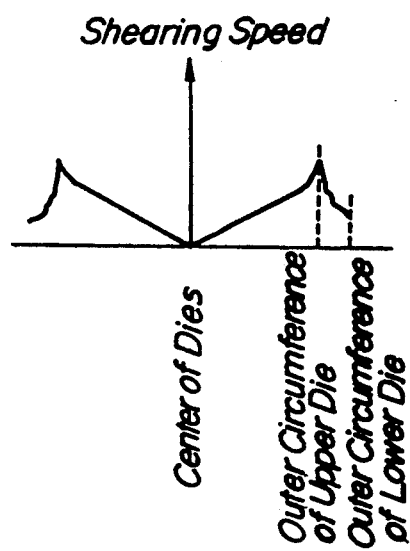
FIG. 3B is a graph showing a relationship between a shearing velocity and a radius of dies constituting the apparatus.
Figure 4A:
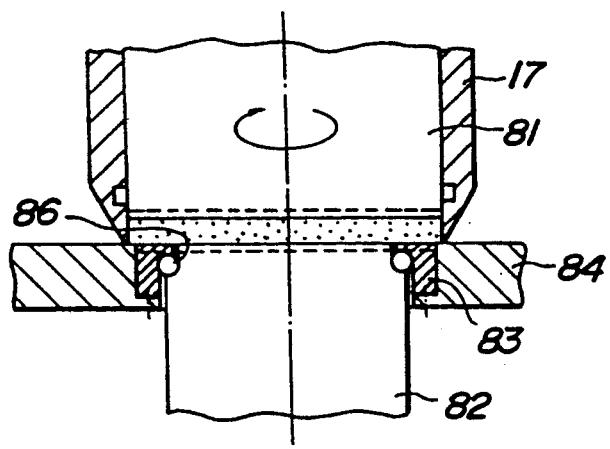
FIG. 4A is a cross sectional view depicting a principle construction of the first aspect of the apparatus for measuring a stress of viscoelastic material according to the invention.
Figure 4B:
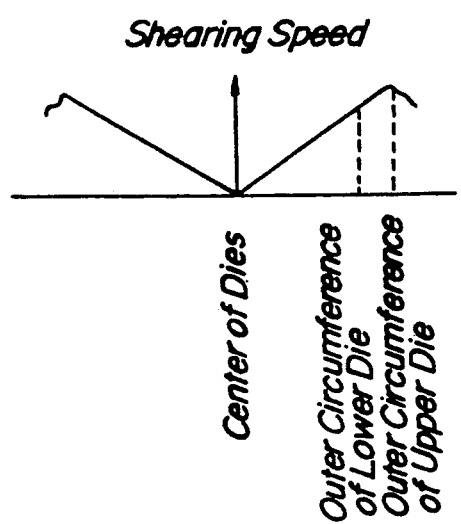
FIG. 4B is a graph showing a shearing velocity and the radii of dies constituting the apparatus.
Figure 5A:
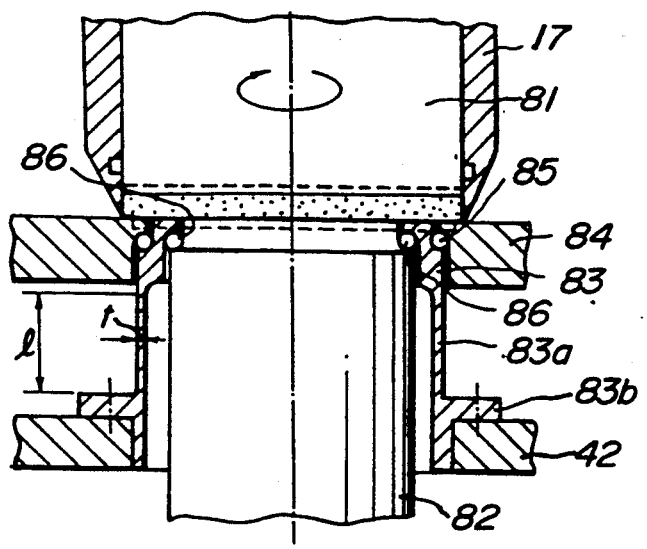
FIG. 5A is a cross sectional view representing the second aspect of the apparatus according to the invention.
Figure 5B:
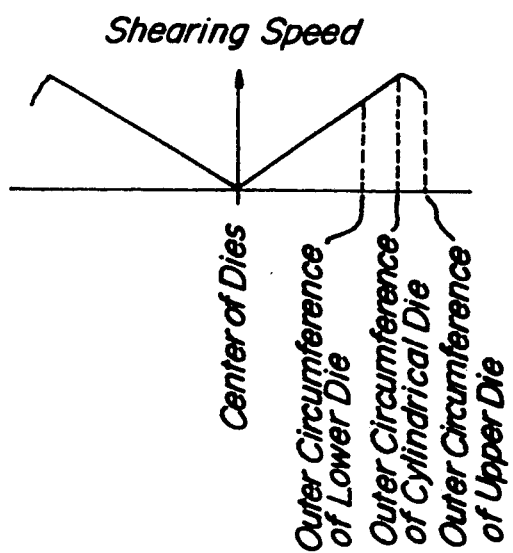
FIG. 5B is a graph showing a shearing velocity and the radii of dies constituting the apparatus represented in FIG. 5A.
Figure 7A:
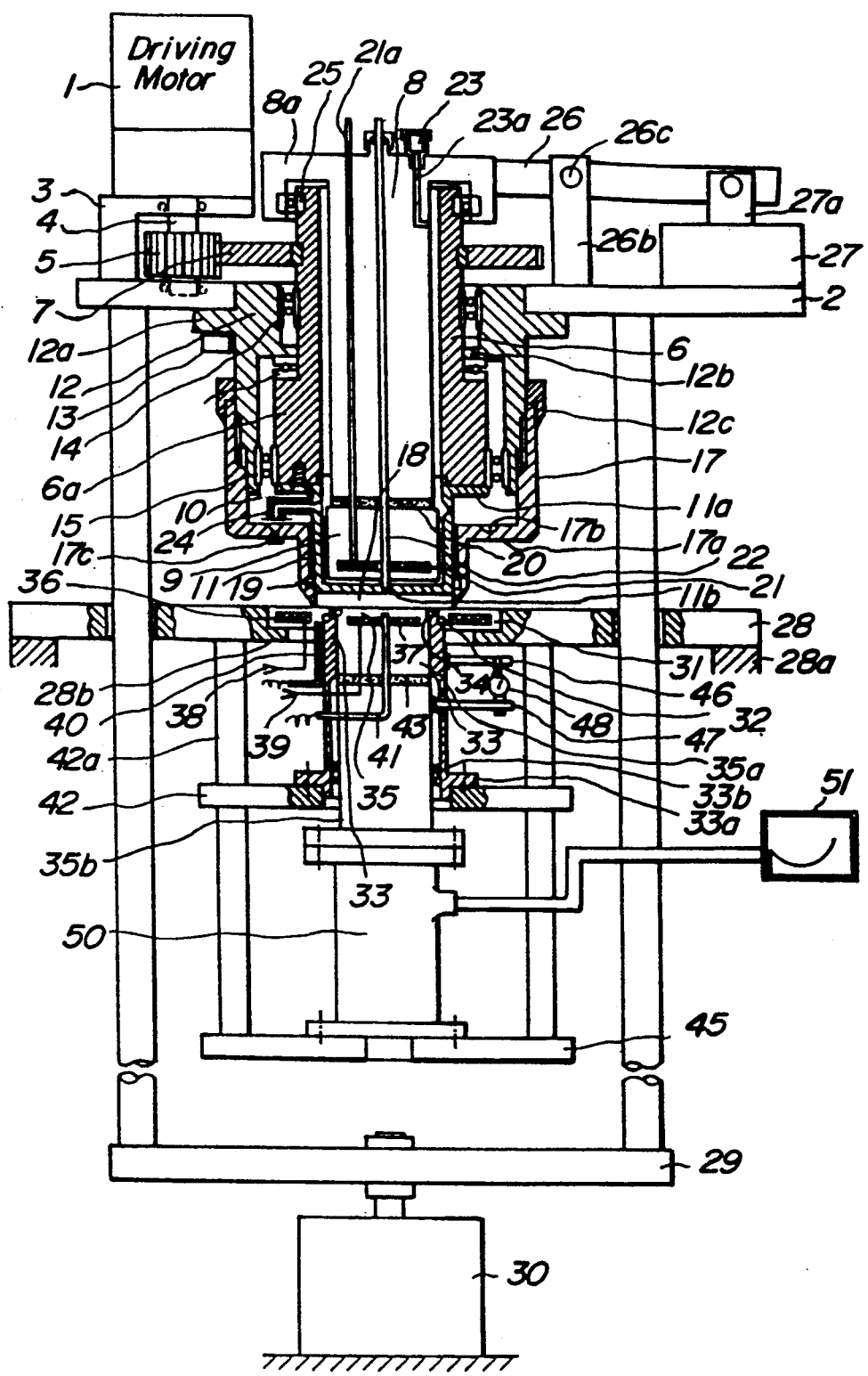
FIG. 7A is a cross sectional view illustrating a construction of a first embodiment of the apparatus according to the invention.
Figure 7B:
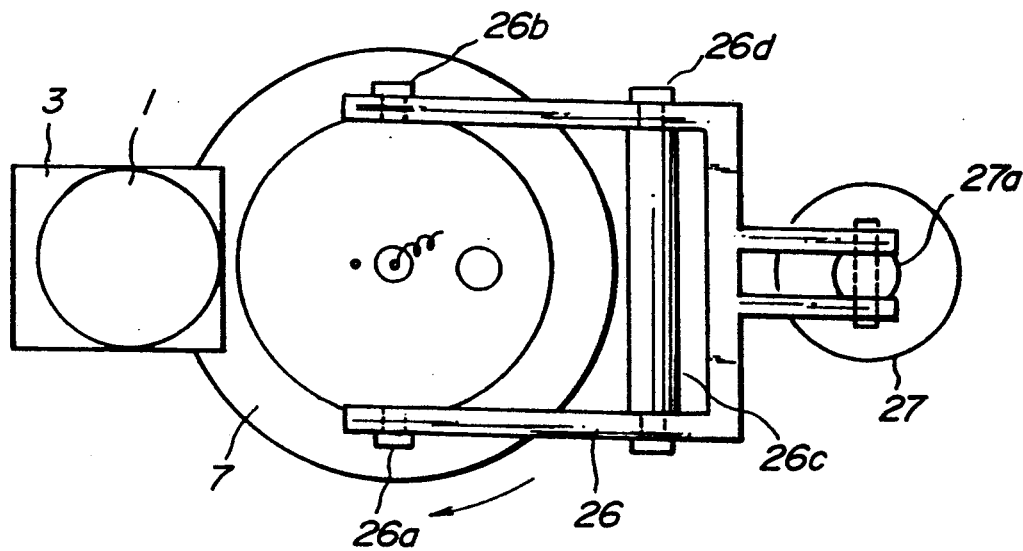
FIG. 7B a plan view thereof.

FIG. 7A shows an entire construction of a first embodiment of the apparatus according to the first, second and third aspects of the invention and FIG. 7B is a plan view thereof.

A motor 1 is provided on a first base plate 2, which is arranged to be movable in a vertical direction, via a supporting plate 3. The rotation of the motor 1 is transmitted to a spur gear 5 via a shaft 4. The spur gear is further made contact with another spur gear 7, which is provided a shaft 6 being arranged on a central portion of said first base plate 2 to be movable in a vertical direction. The shaft 6 has a substantially cylindrical shape having a hollow therein; and a lower part 6a of the shaft 6 is projected outside. In the hollow portion of the shaft 6, is contained an upper die holder 8, on a lower end of which is provided a heater block 9. On the lower end of the shaft 6, is further connected an upper rotational die 11 such that a flange portion 11a is fixed to the projected lower part 6a of the shaft 6 by means of a screw 10. Therefore, the rotation of the motor 1 is transmitted to the upper rotational die 11 via the shaft 4, spur gears 5 and 7 and the shaft 6, so that the shaft 6 and the upper rotational die 11 are arranged to be rotated about the upper die holder 8 and the heater block 9.

Between the shaft 6 and the first base plate 2, is provided a bearing case 12, which has an outer flange portion 12a on the outer circumference thereof and an inner flange portion 12b on the inner circumference thereof. The flange portion 12 is fixed to the lower surface of the base plate 2 by means of a screw 13. The bearing case 12 is connected to the shaft 6 via a slide bearing 14 on the upper portion thereof and via a slide bearing 15 on the lower portion thereof. Further, there is provided a thrust bearing 16 between an upper surface of the projected lower part 6a of the shaft 6 and the inner flange portion 12b of the bearing case 12. On the outer circumference of the bearing case 12, is provided an engaging portion 12c to which an upper part of an upper fixed die 17 is fixed. On an inner surface of the engaging portion 12c, there is provided a screw tap; and the upper part of the upper fixed die 17 is made to contact therewith. The upper fixed die 17 comprises a stage portion 17a and a lower end thereof is extended from the bottom surface of the upper rotational die 11 into a lower direction by a length corresponding to the thickness of a sample to be tested. It should be noted that an inner circumference of the lower extended portion of the upper fixed die 17 and the bottom surface of the upper rotational die 11 form of one part of a sample chamber 18. Further, between the outer circumference of the lower end of the upper rotational die 11 and the inner circumference of the lower end of the upper fixed die 17, is arranged an O-ring 19 to prevent leakage of the sample contained in the sample chamber 18.

On the lower end of the upper die holder 8, there is provided the heater block 9 via a heat insulating material 20. In the vicinity of the lower end of the heater block 9, is embedded an electric heater 21. A temperature detector 22 is provided in the center of the upper die holder 8 to be extended through the upper die holder 8, the heat insulating material and the heater block 9. The top end portion of the temperature detector 22 is extended above a concave portion 11b arranged in the center of the inner bottom surface of the upper rotational die 11. On an upper portion of the upper die holder 8 is provided an inlet 23 for injecting a heating medium in a space formed between the upper rotational die 11 and the heater block 9. A channel 23a is extended from the inlet 23 to a space formed between the upper die holder 8 and the shaft 6 to supply the heating medium into the space formed between the heater block 9 and the upper rotational die 11. In this embodiment, a silicone oil is used as the heating medium because the silicone oil has a large heat resistivity and is chemically stable. On the upper portion of said upper rotational die 11, is provided an outlet 24 to exhaust silicone oil that overflows. Further, on the inner surface of the step portion 17a of the upper fixed die 17, is arranged a groove 17b along the circumference of the step portion 17a to collect the overflow silicone oil. The collected silicone oil is exhausted outside via an exhaust opening 17c which is provided in the step portion 17a. The numerical number 21a represents an electrical lead line which is connected to the heater 21.

A flange portion 8a is provided on the upper end portion of the upper die holder 8 to connect the upper die holder 8 to the upper portion of the shaft 6 via a bearing 25. As clear from FIG. 7B, arms 26 are fixed to the outer circumference of the flange portion 8a of the upper die holder 8 by means of screws 26a and 26b. The arms 26 are further secured to a shaft 27a of a first cylinder 27, which is provided on the first base plate 2. The upper die holder 8, the shaft 6 and the upper rotational die 11 are arranged to be movable in the upper and lower directions by driving the first cylinder 27, since the arms 26 are swung about a shaft 26c thereby. Accordingly the sample can be mounted and removed on and from the sample chamber 18 and the sample chamber 18 can be cleaned.

A stand 28a is set at the height of the lowest end of the upper fixed die 17; a second base plate 28 is supported thereby. A rod-like stand 2a, supporting the first base plate 2, is extended to a connecting plate 29 in the lower direction through the second base plate 28. The lowest end of the stand 2a is fixed to the connecting plate 29 which connects the stand 2a and a shaft of a second cylinder 30. Members constituting the upper dies, the motor 1, the supporting member 3 and the first base plate 2 are arranged to be integrally moved in the upper and lower direction by driving the second cylinder 30. The sample is mounted on and removed from the sample chamber 18 in such manner. The stand 28a, supporting the second base plate 28, is secured to the floor. In the second base plate 28, there is provided a flange portion 28b to which a lower fixed die 31 is fixed.

On the lower surface of the second base plate 28, is further secured a third stand 42a, to which a third base plate 42 and a fourth base plate 45 are provided. On the inner side of the lower fixed die 31, is arranged a free end of a lower outer cylindrical die 33 via an O ring 32. A flange portion 33a provided on the lower end of said cylindrical die 33 is fixed to the third base plate 42. On the inner side of the lower outer cylindrical die 33, is further provided a lower die 35 via an O ring 34. The lower die 35 is fixed to a torque detector 50, which is secured to the fourth base plate 45, via a heat insulating material 43 and a lower die holder 35b. There is provided a bearing 33b between the outer circumference of the lower die holder 35b and the inner circumference of the lower outer cylindrical die 33. The torque detected by the torque detector 50 is recorded by a recorder 51. On the outer circumferences of the lower die holder 35b and the lower outer cylindrical die 33, are arranged arms 46 and 47, respectively. Between these arms 46 and 47, there is arranged an infinitesimal displacement detector 48 to detect a difference in large scale in the displacement of the lower outer cylindrical die 33 and the lower die 31. The difference, for instance, a difference in the rotational amount of the lower outer cylindrical die 33 and the lower die 31, is caused by the shearing force of the sample.

Electric heaters 36 and 37 are embedded in the lower fixed die 31 and the lower die 35, respectively, to keep the temperature of the sample contained in the sample chamber 18 at a predetermined test temperature. These heaters are controlled by a controller (not shown) to heat up the lower fixed die 31 and the lower die 35. The numerical numbers 38 and 39 denote electrical lead wires connecting the controller with the heaters 36 and 37, respectively; the numerical numbers 40 and 41 temperature detectors for detecting the temperatures of the lower fixed die 31 and the lower die 35, respectively.

The sample chamber 18 is formed by the bottom surface of the upper rotation die 11, the inner side surface of the upper fixed die 17, the upper surface of the lower fixed die 31, the upper surface of the lower outer cylindrical die 33 and the upper surface of the lower die 35. The sample is contained in the sample chamber 18; the sample is heated up to the predetermined test temperature by controlling the outputs of the heaters 21, 16 and 37 by an electric power controller (not shown). After heating the sample, the motor 1 is driven to rotate the upper rotational die 11; the shear is given to the sample according to the rotation of the upper rotational die 11. The sample gives a shearing stress to the lower die 35 and the lower outer cylindrical die 33; the lower die 35 and the lower outer cylindrical die 33 are rotationally transformed in proportion to the shearing stress. In the torque detector 50, a counter torque signal generated in accordance with the rotational transformation amount of the lower die 35 and the lower outer cylindrical die 33 is detected. The torque signal is amplified by an amplifier (not shown) provided in the torque detector 50 and then recorded by the recorder 51.

On the lower surface of the upper rotational die 11, the upper surfaces of the lower die 35 and the lower outer cylindrical die 33, which form the sample chamber 18, are provided grooves for preventing to cause a slip of the sample in the sample chamber 18. The upper fixed die 17 is arranged not to be rotated and an existence of the seal 34 does not influence in the torque to be detected for the reason stated in below. Therefore, it may be possible to reduce the exposed area of the seal 34 exposed to the sample chamber 18. Additionally there is not generated a slip of the sample on the upper surface of the lower die 35 and thus it is possible to give a shearing velocity without disorder to the sample.

On the outer circumference of the lower die 35 is arranged the lower outer cylindrical die 33 in order to make the transformation amount of the lower die 35 caused by a rotational transformation amount of the torque detector 50, which is caused by the shearing stress given by the sample, the same as the rotational transformation amount of the lower outer cylindrical die 33 caused by the shearing stress of the sample. Therefore, it is possible to detect the pure rotational torque, which has been given to the torque detecting die by the sample, without being influenced by the elastic transformational torque or the frictional torque of the seal 34.

When the sample is exchanged, the first base plate 2 and the upper dies connected thereto are moved in the upper direction by driving the cylinder 30. As stated in the above, it is possible to exchange the sample more easily by moving the upper die holder 8, shaft 6 and the upper rotational die 11 in the upper direction by means of the cylinder 27 provided on the first base plate 2. The height of the sample chamber 18 is determined by the position where the thrust bearing 16 touches to the flange portion 12a of the bearing case 12. The height of the sample chamber 18 can be changed by loosening the fixing screw 12c, by which the upper fixed die 17 is fixed to the bearing case 12.

Figure 8:
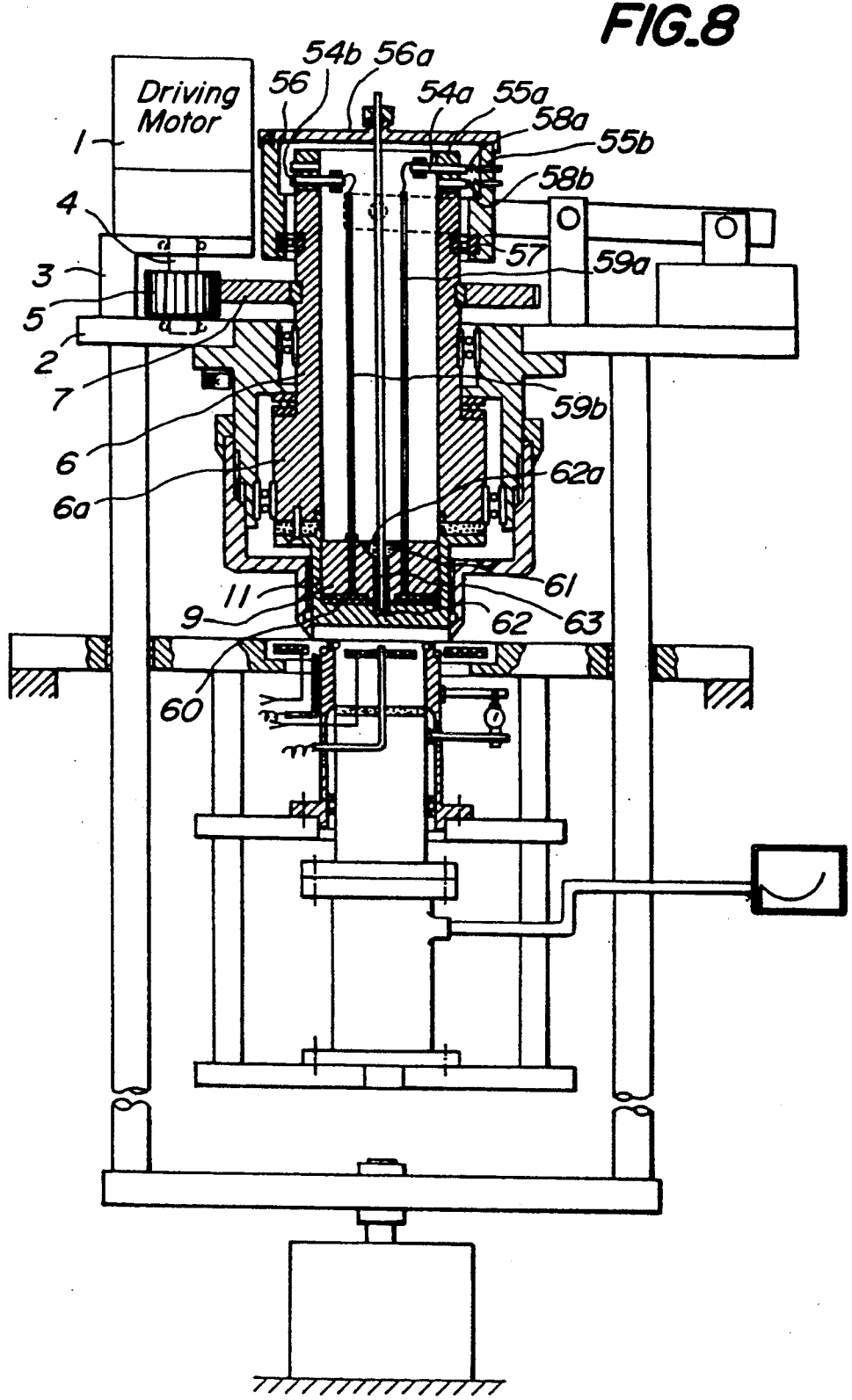
FIG. 8 is a cross sectional view depicting a construction of a second embodiment of the apparatus according to the invention.

FIG. 8 is a cross sectional view showing a second embodiment according to the apparatus of the first and second aspects of the invention. In the second embodiment, the upper die has no double construction. Accordingly the electric power is supplied to the heaters via a slip-ring. But, since the other construction is the same as that of the apparatus shown in FIG. 7A, the explanation therefor is omitted here. It should be noted that the same numerical numbers are applied to the same members as those of the apparatus shown in FIG. 7A.

The rotation of the motor 1 is transmitted to the shaft 6 via the spur gears 5 and 7 to rotate the upper rotational die 11. The bottom surface of the flange portion 6a of the shaft 6 is coupled with the flange portion 11b of the upper rotational die 11 via the heat insulating material 20a by means of the screw 10a. On the bottom surface of the upper rotational die 11, is secured a heater block 11a having heaters 60 on the bottom therein, so that the heater block 11a is rotated in accordance with the rotation of the upper rotational die 11. The shaft 6 is arranged to have a cylindrical hollow therein. In the upper portion of the shaft 6 is embedded two slip rings 54a and 54b via an insulator 55a. A cover 56 surrounding these slip rings 54a and 54b and the insulator 55a is provided on the upper circumference of the shaft 6 via the bearing 57. Through this cover 56 are provided carbon brushes 58a to 58b to contact with the slip rings 54a and 54b. Peripheral portions of the extended holes for arranging the carbon brushes 58a and 58b provided through the cover 56 are closed by an insulating material 55b. One end portion of each slip ring 54a, 54b is projected to inner portion of the shaft 6 to be connected to the electric heaters 60 via lead lines 59a and 59b. In the center portion of the heater block 11a, there is formed a hole 62 in which a heat medium 61 and the temperature detecting device 63 are contained. It should be noted that the hole 62 is extended to the bottom of the heater block 11a. On the cover 56, is provided a cap 56a. The temperature detecting device 63 is extended from the center portion of the cap 56a to the bottom of the hole 62; and the top end portion of the device 63 is arranged to be secured to the center portion of the cap 56a. In the upper portion of the hole 62, is provided a bowl-like portion 62a. The heating medium is contained in the bowl-like portion 62a and the hole 62.

In case that low-melting point metal such as Wood's metal is used as the heating medium, it should be arranged such that the upper rotational die 11 is rotated after the Wood's metal has melted to some degree in order to prevent to make each part of the rotating members out of order. The temperature detecting device 63 is principally provided for detecting the temperature of the upper die on the surface faced to the sample, but the device 63 actually serves to detect the temperature of the heating medium 61 to control the motor 1 so as not to be driven when the temperature of the heat medium 61 is lower that a predetermined temperature.

Figure 9:
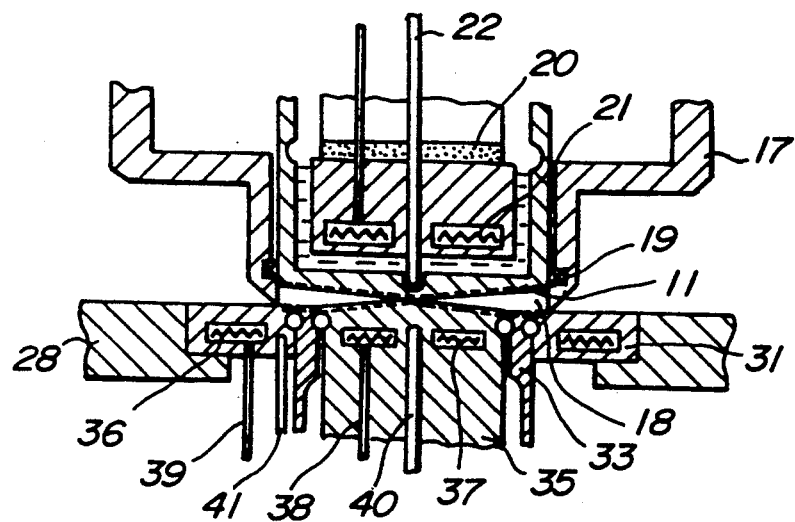
FIGS. 9 and 10 are cross sectional views representing constructions of third and fourth embodiments of apparatus according to the invention.
Figure 10:
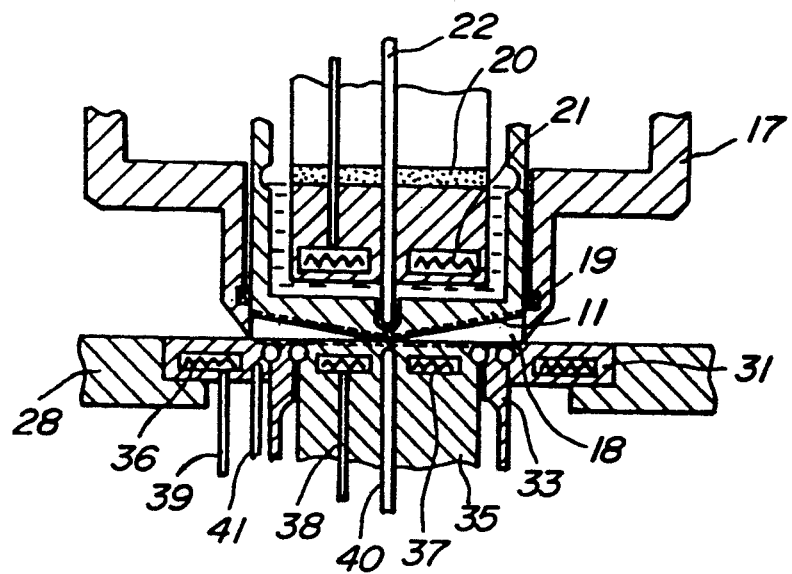

FIGS. 9 and 10 are cross sectional views showing third and fourth embodiments of the apparatus according to the invention. In the third embodiment shown in FIG. 9, the lower surface of the upper rotational die 11 and the upper surface of the lower die 35 are arranged to be conical, respectively. In the fourth embodiment shown in FIG. 10, the lower surface of the upper rotational die 11 is made conical and the upper surface of the lower die 35 is made flat.

Figure 11:
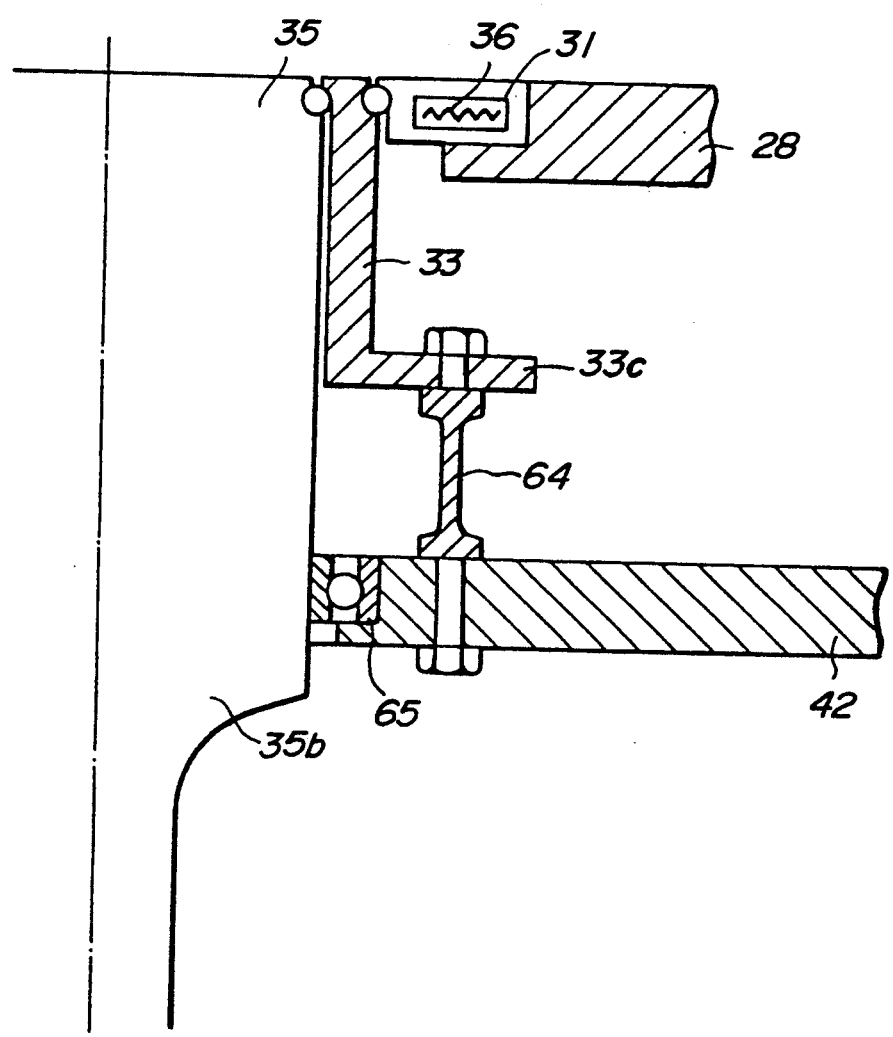
FIG. 11 is a partial cross sectional view showing a modification of the present invention.

FIG. 11 is a modification of the apparatus according to the invention shown in FIGS. 7A and 8A. As clear from FIG. 11, in this modification, the lower end portion of the lower outer cylindrical die 33 is not extended to the third base plate 42, but a flange portion 33c is provided and the flange portion 33c is connected to the third base plate 42 via a plurality of shafts 64. The third base plate 42 is further connected to the upper portion of the lower die holder 35b via a bearing 65. In this variation, an intensity of a shafts 46 with respect to the rotational transformation of the outer cylindrical die 33 can be adjusted so as to make incident the rotational transformation of the lower outer cylindrical die 33 with the lower die 35 by adjusting diameters of the shafts or the number of the shafts to be used.

Figure 12:
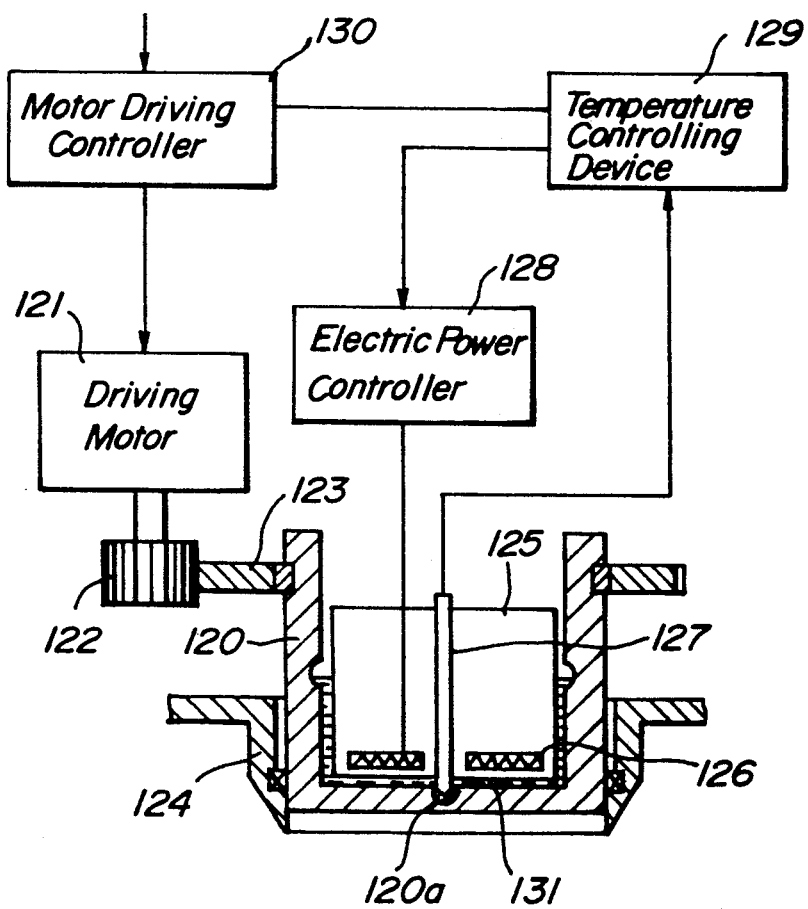
FIG. 12 is a block diagram depicting a temperature controlling system which is applied to the apparatus according to the invention.

FIG. 12 is a block diagram showing a temperature controlling system for controlling the temperature of the rotational member. This system is suitable to apply the apparatus according to the invention. The numerical number 121 represents a driving motor for rotating the rotational driving member 120, 122 and 123 spur gears for transmitting the rotation of the motor 121 to the rotational driving member 120 the rotational driving member, 124 outer fixed die, 125 fixed member (heater block), 126 heaters, 127 temperature detector, 128 an electric power controller, 129 a temperature controller; and 130 represents a controller for controlling the motor 121. Between the rotational driving member 120 and the heater block 125, is contained a Wood's metal 131, which is a low-melting point metal, as a heating medium. The temperature detector 127 is extended through the center portion of the heater block 125. The lower end of the detector 127 is extended to a concaved portion 120a, which is provided on the inner bottom surface of the rotational driving member 120, for collecting the heating medium 131, to detect the temperature of the Wood's metal 131 contained in a space formed between the heater block 125 and the rotational driving member 120.

The temperature of the Wood's metal 131 detected by the detector 127 is supplied to a temperature controlling device 129. In the temperature controlling device 129, the input signal is compared with a predetermined reference temperature of the heating medium 131 to supply a heater control signal to an electric power controller 128, by which the heater 126 is controlled to keep the temperature of the heating medium 131 at a constant desired temperature in accordance with the heater control signal.

Further, in order to prevent rotation of the rotating member before the Wood's metal 131 is melted, a sequence control is conducted. That is to say, a voltage $e_0$, which is corresponding to the temperature detected by the detector 127, is applied from the temperature controlling device 129 to a motor driving controller 130. In the motor driving controller 130, a reference temperature $E_0$ for melting the Wood's metal is compared with the output $e_0$ of the temperature controlling device 129 to control the driving motor 121 such that the motor 121 is allowed to rotate when the reference temperature $E_0$ is equal or larger than the detected temperature $e_0$ ($E_0 \leq e_0$).

In the above mentioned embodiment, the temperature detected by the detector 127 is used for detecting the melting condition of the heating medium, i.e. Wood's metal and the rotation starting point of the driving motor 121 is controlled thereby. However, it may be possible to arrange such that a solid state pressure sensor is immersed in the Wood's metal to detect a variation of the pressure in the Wood's metal when the Wood's metal is melted in order to control the rotating starting condition for the rotation of the driving motor 121.

It should be noted that in case that a liquid or a viscosity liquid is used as the heating medium, it is not necessary to provide the motor driving controller 130.

The temperature controlling system can applied to the apparatus for measuring stress of viscoelastic material as shown in FIG. 7A.

FIG. 13 is a schematic cross sectional view showing a fifth embodiment of the apparatus according to the invention. In this fifth embodiment, there is not provided the lower outer die 33 in the outer circumference of the lower die 35. Therefore, there would be caused some disorder in the detected torque, but the temperature controlling system for controlling the temperatures of the heating medium and the sample is still effective in the fifth embodiment.

Figure 14A:
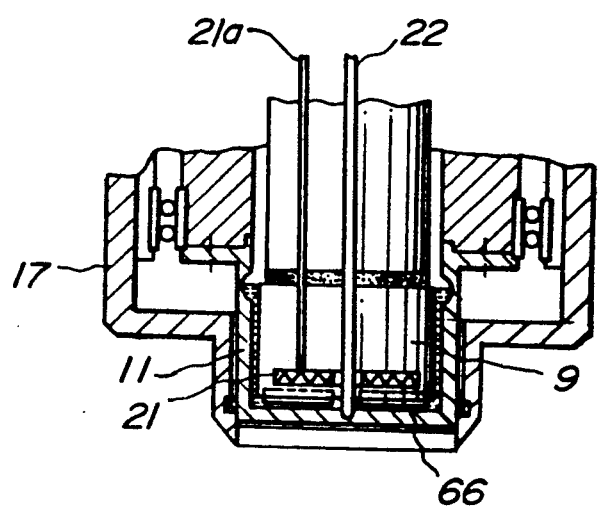
FIGS. 14A and 14B are schematic views representing a modification of a heater block which is preferably applied to the apparatus according to the invention.
Figure 14B:
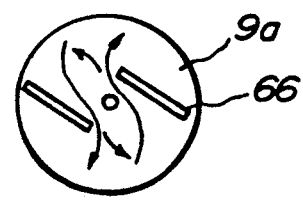

FIGS. 14A and 14B are schematic views illustrating another modification of the apparatus according to the invention. FIG. 14A is a cross sectional view of the device and FIG. 14B is a bottom view of the heater block 9 set in the apparatus. As clear from these figures, there are provided agitation blades 66 on the bottom surface 9a of the heater block 9 in order to increase a heat conductivity of the heating medium contained between the heater block 9 and the rotating driving member 11 and to make a temperature distribution in the heating medium even by agitating the heating medium with the aid of the agitating blades 66. It may be possible to have the same effect in the case that the agitating blades are arranged on the inner surface of the bottom portion of the rotating driving member 11.

FIGS. 15A and 15B are schematic views illustrating another modification of the construction of the heater block 9, which is useful in the apparatus in which the heating medium having a low heat conductivity, such as a silicone oil, is used. FIG. 15A is a cross sectional view of the heater block 9 and FIG. 15B is a bottom view of the heater block 9. When the heating medium having a low heat conductivity is used, it is desired to make the space formed between the heater block 9 and the rotational member 11 as small as possible in order to conduct the heat from the heater block 9 to the rotational member 11 in an effective manner. In this modification, in order to conduct the heat from the heater block 9 to the rotational member in an effective manner, a slit 67 is provided in a spiral manner on the outer circumference surface and the bottom surface of the heater block 9. In such construction, the silicone oil stays in the slit 67, so that it is possible to heat up the heat block 9 as a whole in an even manner. It should be noted that the silicone oil serves as a lube oil to rotate the rotational member 11 smoothly.

Figure 16:
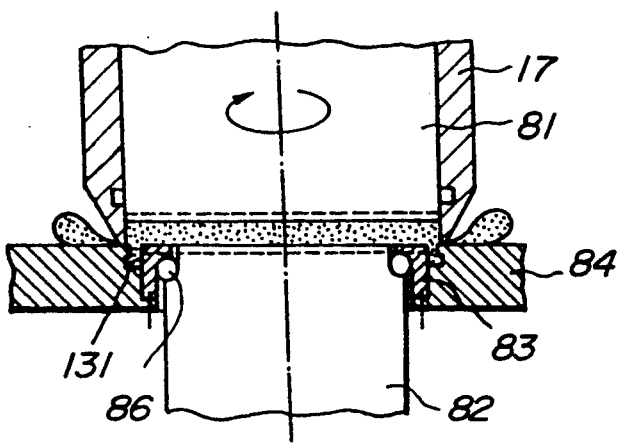
FIG. 16 is a schematic view illustrating a sixth embodiment of the apparatus according to the invention.

FIG. 16 is schematic view showing sixth embodiment of the apparatus for measuring stress of viscoelastic material according to the invention. In this embodiment, in the inner circumference of the lower fixed die 84 are arranged grooves 131 in an opposite manner such that the grooves 131 are connected to the sample chamber 116. Grooves 131 being opposite to each other are provided for the purpose that the sample is constantly left at the lower fixed die side every so often when the sample chamber is opened after the examination has been finished. That is to say, after mounting the sample in the sample chamber 116 and the rotational die 81 is rotated to give a shear to the sample, a portion of the sample is entered into the grooves 115 with the aid of heat generated by the rotation of the rotational die 81 to form lug portions is the sample. Therefore, when the upper dies are lifted up and the sample chamber 116 is opened, the sample is connected to the lower fixed die 84 by means of the lug portions, so that the sample is constantly left at the lower die side.

Figure 17A:
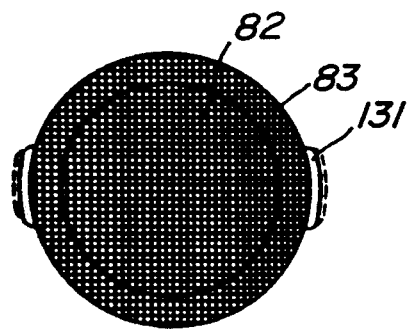
FIGS. 17A and 17B are schematic views depicting the upper surface of the lower die and the lower cylindrical die which are applied to the sixth embodiment.
Figure 17B:
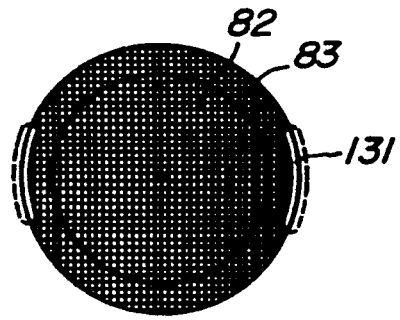

FIGS. 17A and 17B are schematic views illustrating the upper surfaces of the lower die 82 and the lower cylindrical die (torque detecting die) 83 and the grooves 131. It may be possible to locate the grooves 131 on the outer circumference of the lower rotating die 83 or to arrange such that the grooves are spread over the outer circumference and the inner edge portion of the lower cylindrical die 83. However, the grooves 131 should not be arranged in such positions that the torque detecting die 83 is being influenced by the lug portion in detecting counter-torque of the sample.

Figure 18:
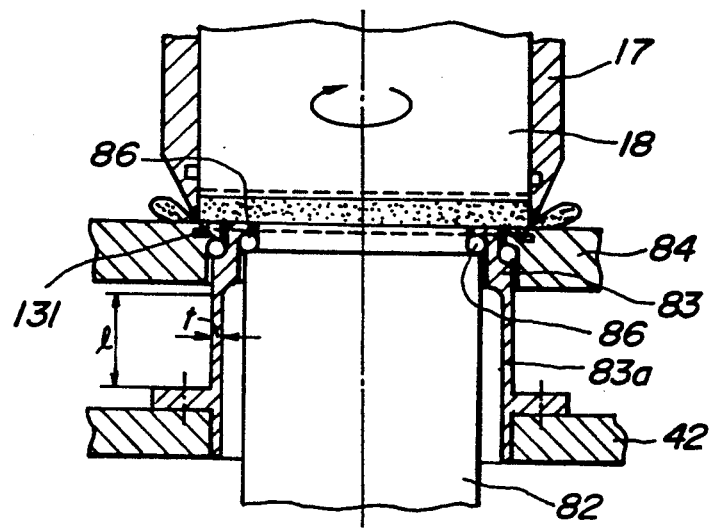
FIG. 18 is a schematic view representing an eighth embodiment of the apparatus according to the invention.

FIG. 18 is a schematic view showing an eighth embodiment of the apparatus according to the invention. In the embodiment, the construction of the grooves is applied to the apparatus according to the second aspect of the invention, in which the lower cylindrical die 83 and the lower rotating die 82 are arranged to be rotated in the same direction by the same angle, as illustrated in FIG. 18.

Figure 19:
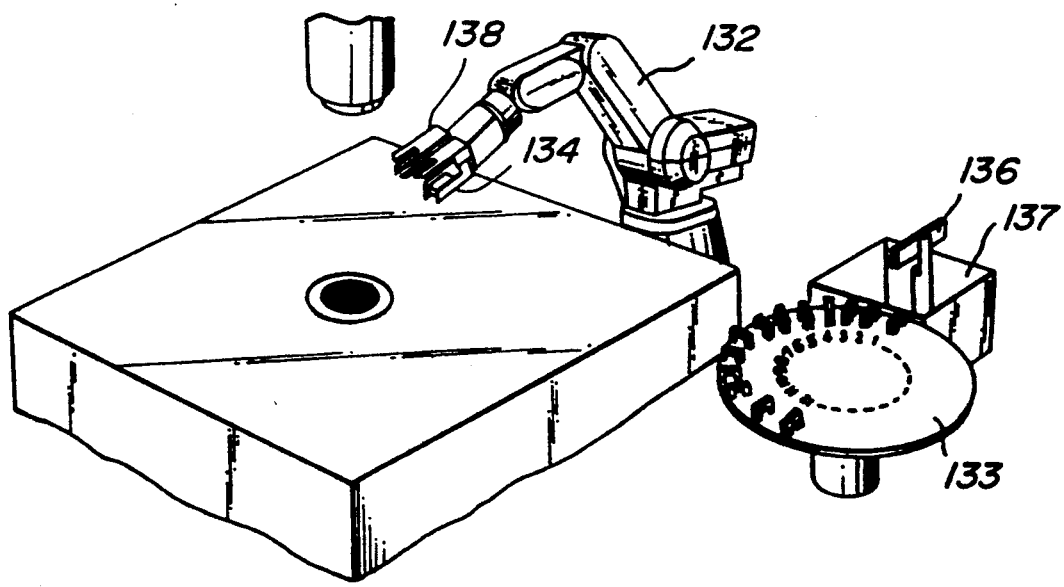
FIG. 19 is a schematic view showing an automatic sample mounting and removing device which is preferably applied to the apparatus according to the invention.

FIG. 19 is a schematic view showing an automatic sample mounting and removing device for applying to the apparatus according to the invention. A miniature robot 132 for use in industrial purposes is used to mount and/or remove the sample on/from the sample chamber of the apparatus.

Each groove 131 provided in the lower die 84 has an L shape viewed from the side, as shown in FIGS. 16 and 18. In other words, the bottom surface of the groove 131 is larger than the upper entrance thereof. Therefore, when the upper dies 17 and 81 are lifted up to open the sample chamber, the grooves 131 serve to leave the sample on the lower die side.

Figure 20:
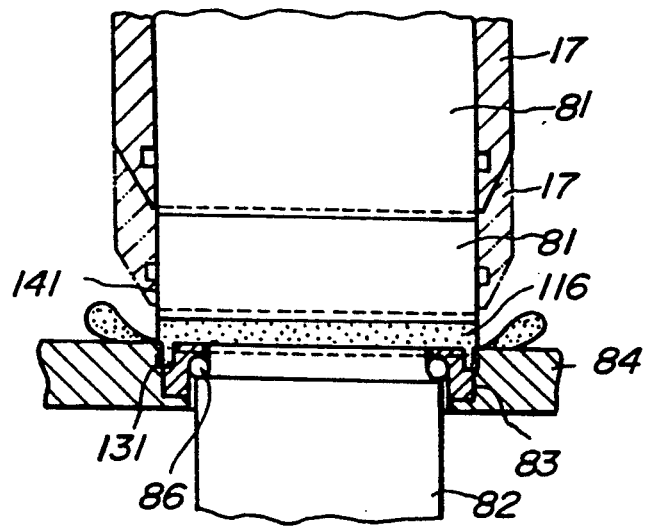
FIG. 20 is a schematic view showing a condition where the sample chamber is open to remove the sample contained in the sample chamber.

On the periphery of a turntable 133, a plurality of samples are prepared as shown in FIG. 19. The sample is transferred by a hand 134 of the robot 132 from the turntable 133 to the apparatus to be mounted on the lower rotational die thereof. After measurement, the sample is, as stated in the above, left on the lower die side due to the lug portions formed in an opposite manner in the sample. The measuring apparatus is arranged such that when removing the sample, the upper fixing die 17 is lifted first and then the rotational die 81 is lifted. The condition is shown in FIG. 20. When the upper fixed die 17 is lifted in an upper direction, the side surface of the sample is exposed outside and then the rotational die 81 is lifted up with the fixed die 17. Thus an area where the sample is contacted with the upper dies 17 and 81 becomes so small that the sample is apt to be left at the lower die side. Furthermore, during the measurement, sample leaks into a rotational contour portion 141 between the inner side surface of the upper fixed die 17 and the outer side surface of the upper rotational die 81. In the apparatus, since the upper fixed die is first lifted up, the leaked sample is exposed outside before the upper rotational die 81 is lifted up. Therefore, the sample is apt to be left at the lower die side without being affected by the leaked sample.

Figure 21:
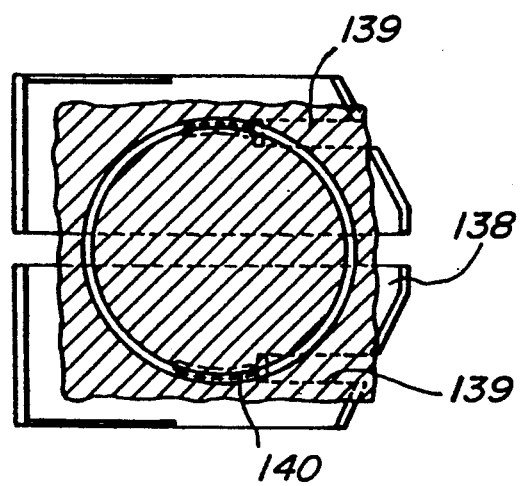
FIG. 21 is a schematic plan view illustrating a sample holding plate for removing the sample, which is provided on a miniature robot.

Hithertofore, after measurement, a sample holding member having a pin is used for removing the sample. That is to say, the pin of the member is put through the sample to remove it from the sample chamber. However, in case the sample is non-vulcanized rubber or semi-vulcanized rubber, even if the pin is put through the sample, the sample is torn by the pin because the sample has a great viscosity. In order to solve this problem, the sample mounting/removing device applied in the present invention is arranged such that the arm of the miniature robot 132 comprises a plate 138 whose area is larger than an area of the torque detecting dies 82 and 83. FIG. 21 is a schematic plan view of the plate 138 of the robot 132. When removing the sample, the plate 138 is inserted in a border surface between the sample and the torque detecting dies 82 and 83 so as to support the sample as a whole by the plate 138 as shown in FIG. 22. By such construction, the part of sample being caught by the groove 131 is easily pealed from the lower dies 82 and 83 as well as the sample proper. The sample as a whole is held on the plate 138 to be removed.

The plate 138 comprises a couple of plate members and in each there is provided a recess 139 as shown in FIGS. 21 and 23. Therefore, until the plate 138 is inserted into the border between the sample and the lower dies 82 and 83 to some degree, the lug portions of the sample caught by the grooves 131 are not pealed from the die; thus the plate 138 is certainly inserted into the border thereby.

After measurement, the sample is thrown away into a trash box 137 by releasing the couple of plate members on the trash box 137. In case the sample has a great viscosity, when the sample is thrown away, the sample adheres to the plate members, so that the sample does not fall down to the trash box 137. In order to make the sample fall down into the trash box 137, a scraper 136 is provided in the trash box 137, as shown in FIG. 19. When the sample holding member 118 is moved onto the trash box 137, the sample is surely thrown away by the scraper 136.

FIG. 22 is a schematic view showing a condition that the holding plate 138 is inserted between the sample and the lower dies. It should be noted that the plate 138 may be inclined to be inserted in order to increase the effect thereof.

Furthermore, it is possible to measure automatically the stress of the sample by applying the above sample mounting and removing device to the measuring apparatus according to the invention. The sequential operations are as follows: start switch ON→holding the sample No. 1→mounting the sample on the lower dies→lifting down the upper dies→rotating the motor (experiment is started)→stopping the motor (experiment is finished)→outputting the data→the cylinder for lifting up the upper fixed die ON→the cylinder for lifting up the upper rotational die ON→the sample is left at the lower die side→removing the sample→disposing the sample→holding the sample No. 2.

As stated above in detail, according to the first aspect of the present invention, the outer cylindrical die is provided in addition to the upper die, the lower die; the surfaces of these dies forming of the sample chamber has a configuration to prevent the slip of the sample in the sample chamber. The diameter of the upper rotational die is arranged to be larger than the diameter of the outer cylindrical die. The upper fixed die is arranged not to be rotated therefore, the slip of the sample can be prevented in an effective manner and the shearing speed without disorder can be applied to the sample all over the torque detecting lower dies.

Further, according to the second aspect of the present invention, the torque detecting lower die and the outer cylindrical die arranged therearound are arranged to be rotationally displaced in the same direction by the same angle. Therefore, the sealing member arranged between the lower die and the outer cylindrical die is rotated in accordance with the deviation of the lower die and the outer cylindrical die. Thus, the actual torque can be detected without being influenced by the elastic transformation torque or the confliction torque of the sealing member.

Furthermore, according to the third aspect of the present invention, the upper die is arranged to be a double construction, in other words, the upper die comprises a rotational member and the fixed member, and the heating means is provided in the fixed member. Therefore, it is possible to supply the electric power to the heating means without using a slip ring. Thus, it is possible to decrease the maintenance in the apparatus because there is no possibility that the slip ring is out of order due to the corrosion, dust, etc, of the slip ring. In the third invention, in the space between the rotational member and the fixed member is contained a heating medium to control the temperature of the rotating member via the heating medium. Therefore, it is possible to control the temperature of the rotating member in a uniform manner.

Moreover, in accordance with the fourth aspect of the present invention, the apparatus further comprises the sample mounting and removing device, and a plurality of grooves are provided in an opposite manner in the outer cylindrical die and/or the lower fixed die such that the grooves are connected to the sample chamber. Therefore, in the fourth embodiment, the sample can be automatically mounted on the sample chamber and removed therefrom, and further removed. Furthermore, in the fourth aspect, it is possible to mount and remove the sample on and from the sample chamber automatically and continuously without reference to the condition of the viscosity of the sample.

What is claimed is:
1. An apparatus for measuring stress of viscoelastic material, comprising:
   an upper die;
   a lower die;
   a rotating means for giving a rotation one of said upper and lower dies; and the die, which is given the rotation, constituting a rotational die;
   a torque detecting means for detecting a counter torque given to the other one of said upper and lower dies; and the other die constituting a torque detecting die;

an outer cylindrical die being provided around an outer surface of the torque detecting die, a sample chamber for containing a sample; and upper and lower surfaces of the sample chamber being formed by said upper and lower dies and said outer cylindrical die;

surfaces, forming the upper and lower surfaces of the sample chamber, of said upper and lower dies and said outer cylindrical die being arranged to have configurations for preventing slipping of the sample contained in the sample chamber;

a diameter of the rotational die being arranged to be larger than a diameter of said outer cylindrical die;

a fixed die being provided on outer circumference of said rotational die, a part of inner surface of said fixed die forming of a side surface of said sample chamber.

2. An apparatus for measuring stress of viscoelastic material according to claim 1, wherein:

said outer cylindrical die and said torque detecting die are arranged to be rotated in the same direction by the same degree with the aid of a shearing stress given by said sample contained in the sample chamber.

3. An apparatus for measuring stress of viscoelastic material according to claim 1 or 2, wherein:

both a bottom surface of said upper die and an upper surface of said lower die, which are arranged to be opposite to each other, are arranged to be flat.

4. An apparatus for measuring a stress of viscoelastic material according to claim 1 or 2, wherein:

at least one of a bottom surface of said upper die and an upper surface of said lower die, which are arranged to be opposite to each other, is arranged to be conical.

5. An apparatus for measuring stress of viscoelastic material, comprising an upper die comprising a rotational member and a fixing member;

a lower die;

a rotating means for giving a rotation to said rotating member of said upper die;

a torque detecting means for detecting a countertorque given to the lower die;

a sample chamber for containing a sample; and a part of the sample chamber being formed by said upper and lower dies;

a heating means for heating up the sample contained in the sample chamber being arranged in said fixed member of said upper die; and a heating medium being contained in a space formed between said rotating member and said fixing member of said upper die; wherein the heating medium serves to provide uniform heating to the sample and lubricate the rotational member with respect to the fixed member;

a temperature controlling means for controlling the temperature of said sample contained in the sample chamber being arranged such that the temperature of the sample is controlled by said heating means with the aid of said heating medium.

6. An apparatus for measuring stress of viscoelastic material according to claim 5, wherein:

an outer cylindrical die is arranged around an outer circumference of said lower die; an upper surface of said outer cylindrical die, which forms one part of said sample chamber, comprises such a configuration that a slipping of the sample is prevented in said sample chamber; and a diameter of said upper die in arranged to be larger than a diameter of said outer cylindrical die.

7. An apparatus for measuring stress of viscoelastic material according to claim 6, wherein:

said outer cylindrical die and said lower die are arranged to be rotated in the same direction by the same angle with the aid of a shearing stress given by said sample contained in the sample chamber.

8. An apparatus for measuring stress of viscoelastic material according to claim 5, wherein:

said heating medium is a metal having a low melting point.

9. An apparatus for measuring stress of viscoelastic material according to claim 6, wherein:

said heating medium is a metal having a low melting point.

10. An apparatus for measuring stress of viscoelastic material according to claim 7, wherein:

said heating medium is a metal having a low melting point.

11. An apparatus for measuring stress of viscoelastic material according to claim 5, wherein:

both a bottom surface of said upper die and an upper surface of said lower die, which are arranged to be opposite to each other, are arranged to be flat.

12. An apparatus for measuring stress of viscoelastic material according to claim 6, wherein:

both a bottom surface of said upper die and an upper surface of said lower die, which are arranged to be opposite to each other, are arranged to be flat.

13. An apparatus for measuring stress of viscoelastic material according to claim 7, wherein:

both a bottom surface of said upper die and an upper surface of said lower die, which are arranged to be opposite to each other, are arranged to be flat.

14. An apparatus for measuring stress of viscoelastic material according to claim 5, wherein:

at least one of a bottom surface of said upper die and an upper surface of said lower die, which are arranged to be opposite to each other, is arranged to be conical.

15. An apparatus for measuring stress of viscoelastic material according to claim 6, wherein:

at least one of a bottom surface of said upper die and an upper surface of said lower die, which are arranged to be opposite to each other, is arranged to be conical.

16. An apparatus for measuring stress of viscoelastic material according to claim 7, wherein:

at least one of a bottom surface of said upper die and an upper surface of said lower die, which are arranged to be opposite to each other, is arranged to be conical.

17. An apparatus for measuring stress of viscoelastic material according to claim 6, further comprising:

a detecting means for detecting the fact that the metal having a low melting point has been melted;

a controlling means for controlling the rotation of said rotating member of the upper die such that when the fact that the metal having a low melting point has been melted is detected by said detecting means the rotating member starts to be rotated.

18. An apparatus for measuring stress of viscoelastic material according to claim 5, wherein:

an agitating flap is provided on a bottom surface of the rotating member of the upper die to agitate said heat medium contained in the space between the rotating member and the fixed member of the upper die.

19. An apparatus for measuring stress of viscoelastic material according to claim 5, wherein:
   a groove is provided on side and bottom surfaces of the fixing member for containing said heat medium therein.

20. An apparatus for measuring stress of viscoelastic material according to claim 1 or 5, further comprising:
   a sample mounting and removing means for mounting and removing automatically the sample in and from the sample chamber;
   a plurality of grooves being provided in an outer circumference of said outer cylindrical die in an opposite manner; and the grooves being arranged so as to be connected to the sample chamber.

21. An apparatus for measuring stress of viscoelastic material according to claim 20, wherein:
   the sample is removed from the sample chamber under a condition that said rotating member or the torque detecting die and said outer cylindrical die are moved in a vertical axis of the apparatus.

22. An apparatus for measuring stress of viscoelastic material according to claim 20, wherein:
   said sample mounting and removing means comprises a sample holding member comprising a plate-like shape; and
   an area of said holding member is larger than an area of the surface of torque detecting die.

* * * * *